(12) United States Patent
Bullis

(10) Patent No.: US 6,524,248 B1
(45) Date of Patent: Feb. 25, 2003

(54) ABERRATION CORRECTION BY MEASUREMENT AND SUPPRESSION OF DISTORTION WAVES

(76) Inventor: James K. Bullis, 1155 Pimento Ave., Sunnyvale, CA (US) 94087

( * ) Notice: Subject to any disclaimer, the term of this patent is extended or adjusted under 35 U.S.C. 154(b) by 0 days.

(21) Appl. No.: 09/974,114

(22) Filed: Oct. 9, 2001

(51) Int. Cl.$^7$ ................................. A61B 8/00
(52) U.S. Cl. ..................... 600/437; 600/442
(58) Field of Search ................ 600/437, 440, 600/441, 443, 442, 447–454, 458; 76/625, 626; 367/7, 11, 130, 138; 128/916

(56) References Cited

U.S. PATENT DOCUMENTS

| | | | |
|---|---|---|---|
| 4,630,612 A | * 12/1986 | Uchida et al. | 600/441 |
| 5,935,068 A | 8/1999 | Zhu et al. | |
| 6,223,594 B1 | 5/2001 | Langdon et al. | |
| 6,305,225 B1 | * 10/2001 | Bae et al. | 73/602 |
| 6,474,164 B1 | * 11/2002 | Mucciardi et al. | 73/602 |

OTHER PUBLICATIONS

Zhu et al, Modeling measurement and correction of wavefront distortion produced by brust specimens, 1994 ultrasonics symposium, p 1613.

O'Donnell et al. Aberration Correction on a two dimensional phased array, 1991 ultrasonics Symposium, p 1190.

Liu et al., Correction of Ultrasonics wavefront distortion using back projection, Journal of Acoustic Sx. Aug. 94.

Zhu et al, wavefront Amplitude Distortion, Journal of Acoustic Society 96 (1), Jul. 1994, pp 1–9.

* cited by examiner

*Primary Examiner*—Marvin M. Lateef
*Assistant Examiner*—Ali M. Imam

(57) ABSTRACT

The present invention solves a problem that has been a barrier to development of high resolution ultrasonic imaging. It is based on an analysis that formulates the 5 problem of wave propagation in an inhomogeneous medium as a summation of an ideal wave and distortion waves. This analysis then leads to an apparatus that includes a forward propagation apparatus that enables measurement of the distortion waves and determination of corrections that are applied to originally received signals such that the ideal wave is left as the only basis for the final output signal. After signals are corrected, basic beamforming processes work as if the propagation medium was homogeneous such that ideal high resolution performance is achievable. The method is generally useful for improving any form of wave propagation system that is disturbed by inhomogeneities in the medium.

38 Claims, 9 Drawing Sheets (a)

(b)

ABERRATION CORRECTION BY MEASUREMENT AND SUPPRESSION OF DISTORTION WAVES

This patent document contains material that is subject to copyright protection. Facsimile reproduction is allowed of the patent document or the patent disclosure as it appears in the Patent and Trademark Office patent file or records as allowed by US patent law, but otherwise all copyright rights are reserved.

CROSS REFERENCE TO RELATED APPLICATIONS

Not applicable.

BACKGROUND OF THE INVENTION

This invention relates to receiving and focusing of a radiating wave field that propagates in a medium, specifically where that medium causes wave field distortions that degrade quality of focus. Example applications in the field of the invention include ultrasonic medical imaging, seismic prospecting, ultrasonic industrial inspection, radar, sonar, and optics.

An ideal medium for propagation of radiating waves is free space where electromagnetic waves propagate at precisely known speed without distortion. Devices that utilize wave propagation in a medium that is less perfect than this ideal, are subject to a variety of limitations. There are many ways that a medium can be imperfect. It can attenuate signals, it can have propagation speeds that are inaccurately known, and it can be inhomogeneous. Wave fields are focused using an aperture where the quality of focus depends on characteristics of the medium and characteristics of equipment that implements the aperture. A variety of measures are needed to compensate for medium effects to improve quality of focus, but an especially difficult problem is presented when the medium is inhomogeneous.

In discussing wave fields, it is common to speak of wavefronts to help in intuitive understanding of a very complicated physical process. A wavefront is defined to be a surface that contains points of equal phase. A simple wave field has many possible wavefronts, but only one is pictured. However, when this discussion refers to wavefront shape or to modifying wavefront shape, all possible wavefronts are assumed to be so shaped or so modified. References made here to a wavefront are intended to be references to a wave or a wave field by implication. Changing amplitude of a wavefront means that the wave system represented by that wavefront is proportionally changed in amplitude. The term phase is also somewhat inadequate where a single frequency is not utilized. Here a wavefront refers to points at a similar position in a function that causes a wave, such as a leading edge of a pulse or a first peak. For purposes of the present specification, wave speed is the speed of a point on the wavefront, under either of these definitions of wavefront. Wavefronts are frequently described here as spherical surfaces which means that they are sections of a surface of a sphere. When shown as a three dimensional drawing these wavefronts are indicated with a wire mesh that describes the surface. In two dimensional drawings they are indicated by a curved line which is intended to mean a spherical surface, unless otherwise stated.

Waves and wavefronts are a form of signals as are electrical voltage variations in wires and samples of voltages that are in computers. All these forms represent information.

Inhomogeneous problems are significant in ultrasonic imaging in a three dimensional volume such as the human body. It is known that sound speed variations in human tissue can cause significant wavefront distortion over an aperture extent. Such spatial variations tend to defeat the basic focusing function of the aperture because this focusing function depends on a predicted wavefront shape for points in the focus zone and well formed wavefront shapes for wavefronts that come from any point outside the focus zone. Wavefront distortion causes amplitude reduction of a focused signal to be reduced in amplitude, widening of a focal zone (a beam), and increased response for points outside the focal zone.

High resolution is critical to viewing disease processes, but it is widely believed in the field of ultrasonic imaging that aberration effects of inhomogeneous media would limit usefulness of high resolution devices. In ideal media, resolution improves with the use of shorter wavelengths or larger aperture transducers, but in human tissue, which is inhomogeneous, the use of such measures is expected to lead to aberrations that would prevent full benefits that might otherwise be realized (M. O'Donnell and P. Li, "Aberration correction on a two-dimensional anisotropic phased array," 1991 Ultrasonics Symposiun, p1190, IEEE). Although detailed study of past experimental work reveals that spatially uniform attenuation that strongly varies as a function of frequency is also a significant limitation of large aperture devices, the aberration problem remains as a significant barrier to development of high resolution ultrasonic systems.

Inhomogeneous conditions cause degradation of a response function, where that response function describes performance of a transducer system. There can be a transmitting response, which is a measure power as intensity as a function of a spatial dimension or there can be a receiving response, which is a measure of sensitivity as a similar function. Reciprocity usually applies so a transducer response is the same for either direction. Where there is a strong peak in the response function, a main beam is established. In receiver terms, the key degradation issue is the relative strength of a signal that comes from points within a focal zone as compared with the strength of an off-beam signal that comes from points outside the focal zone. Off-beam response is often called sidelobe response, though there can also be a grating lobe response. Terminology tends to be inadequate in practice. It becomes particularly problematic when it leads to use of analytical methods that were developed for ideal media.

Understanding of propagation in a medium that is inhomogeneous requires a meaningful description in terms that can be mathematically analyzed. A common model in the field of medical ultrasonic imaging addresses irregular sound speed variations, where such variations cause wave arrival times at a receiving aperture to deviate from the ideal shape. Arrival time is represented by wavefront shape as it is immediately approaching a receiving aperture. Sound speed variations over the propagation path cause wavefronts to distort, but if accurate time corrections could be ascertained to compensate for the variations of sound speed, the main beam response would be restored. FIG. 1(a) shows as reference an ideal wave 2 propagating from a source that is approximated as a point 11 to a receiver 3 in a homogeneous medium 1 without distortion to cause received signals 4. FIG. 1(b) is comparative illustration for imperfect media 8 that shows a wave perturbing effect 7 of a localized material 5 that varies wave speed, where compensation material 6 is inserted as a lump that would reverse the initial variation of wave speed. In ultrasonic systems, the actual compensating process would be handled as an electronic process after reception of received signals 4. In optical systems, the use of corrective material is a common way to correct for lens errors, which have much the same effect.

This comparative illustration of FIG. 1(b) also shows a blockage 9 that distorts the actual wave by leaving a gap 10 where wave amplitude is zero. For relatively large blockage shown the gap 10 projects geometrically such that the propagated wave 70 proportionately contains a similar gap 71. Artificially filling in the gap is not inconceivable in simple conditions where signals are simply provided to establish uniformity, but in general it is difficult to know what signal is needed. Repairing this gap by time corrections is not conceivable since there is no wave energy to work with. Though it might seem innocuous, the gap is a cause of distortion of significance that is comparative to an uncorrected speed distortion effect. Coherent relationships of multiple gaps make them far more significant than relatively random speed distortion effects.

While this depiction of the problem of FIG. 1 shows relatively large irregularities, there is concern for many small irregularities often exist in an actual imaging situation. Simple projection to portray propagation effects becomes less reasonable for small gaps.

The general approach of applying time adjustments to correct for sound speed variations is valid for sound speed variations that are sufficiently large and slowly varying, and sufficiently close to the receiving aperture. Small to medium localized speed variations that occur in large numbers tend to cause problems with this approach. Attempts have been made to accommodate irregularities that are significantly separated from the receiving aperture using a method called back-projection (Liu and Waag, "Correction of ultrasonic wavefront distortion using backprojection and a reference waveform method for time shift compensation," (Journal of the Acoustic Society of America, 96 (2) August 1994) to establish a surface where time adjustments would be valid, but even if proper time corrections were found which effectively enhance main beam response, the same corrections would only be approximately useful to control off-beam response. Even with these limitations, the time correction approach has been the primary approach, and the basis of many inventions, of the ultrasonic community for many years. A history of development work by the ultrasonic community is discussed in detail in the background given by Langdon et al. U.S. Pat No. 6,223,599. In spite of these widespread efforts, nothing has been sufficiently effective or efficient that it has been made available in commercial medical equipment.

Although the mainstream view is that time correction is required to compensate for aberrations, other approaches have been considered. Zhu and Steinberg suggested large 2D apertures for suppressing random effects (Zhu and Steinberg, "Wavefront amplitude distortion," Journal of the Acoustical Society of America 96 (1) July 1994, pp1–9). Ultimately, Zhu et al. U.S. Pat. No. 5,935,068 disclosed a compression algorithm for suppression of aberration effects, though this would primarily act on a different form of distortion that is variation of amplitude rather than simple time of arrival variations. Zhu et al. attribute variation of amplitude primarily to refraction effects. Langdon et al. U.S. Pat. No. 6,223,599 B1 asserted benefits of harmonic signals which would depend on short wavelength propagation.

Zhu and Steinberg discuss scattering issues (Zhu and Steinberg, "Modeling, measurement and correction of wavefront distortion produced by breast specimens, 1994 Ultrasonics Symposium, p1613, IEEE). Presumably this relates to diffraction processes, though their formulations (equations 1 and 2 of above reference) differ from the traditional approach to scattering. In any case, their small particle scattering model is insufficient to elucidate coherent aspects of scattering. Physiology shows that typical structure of breast tissue, as an example, includes lumps that are well beyond the size where the small particle model is valid. While Zhu and Steinberg consider such larger lumps (FIG. 5 of above reference), they consider these in terms of refraction alone.

Acoustic holography has been made to operate on the basis that when a general illuminating wave in a medium encounters irregularities in that medium, secondary waves are produced that can be individually determined and used to produce images.

The concept of an incident field and a scattered field is commonly used in physics and engineering to formulate problems where localized impedance and attenuation irregularities disturb waves. However, it appears that the general approach to correcting aberrations caused by wave speed variations is to find ways to reverse wave speed variations, as with eyeglasses. This approach seems to have dominated efforts by the academic and industrial ultrasonic research community to solve this problem for 15–20 years.

SUMMARY OF THE INVENTION

A general theory of aberrations in inhomogeneous media has been developed that formulates the effect of an aberration as a combination of an ideal wave and distortion waves. The aberrations are contained in a material that is otherwise homogeneous, to form the inhomogeneous media. This theory accommodates localized disturbances that include wave propagation speed variations as well as attenuation variations and impedance variations. An analysis method based on this formulation of the aberration problem has been used to understand aberration effects and to compute the characteristics of ideal waves and distortion waves as they undergo forward propagation processes. Apparatus was then envisioned that is structured to suppress the distortion waves. Rather than adjusting for wave speed variations as is typically done, the resulting devices seek to measure and eliminate distortion waves to leave ideal waves approximately intact. This is a unique type of spatial filter.

An example of such apparatus is a wave propagation device that includes an intended wave source of an initial spherical wave field, and a first receiving aperture. The initial spherical wave field is an ideal wave that propagates from source to the first receiving aperture, in a medium that contains irregularities that are distributed over a volume of the medium. The irregularities distort the ideal wave and each distortion results in a wave field that is equivalent to an additive combination of at least one distortion wave and a continuation of the ideal wave. Waves are sensed over the first receiving aperture surface to produce first received signals. Forward propagation is provided that allows any distortion wave to expand as a secondary spherical wave. This forward propagation takes place in a clear medium that allows any such distortion waves to expand without further distortion. It is then possible to measure the expanded distortion waves using a second receiving aperture device. Distortion wave measurements are then used to determine correction signals that are applied to the first received signals to eliminate effects of the distortion waves. Then a summation of corrected first received signals is carried out that focuses on the source of the initial spherical wave field. This summation now operates on signals that are caused only by the ideal wave. Reception of signals from the intended wave source is thus enhanced. The process works for many irregularities in the medium.

Importance of the invention increases significantly in the presence of a displaced, second source of a second spherical wave field that is also an ideal wave. It is critical in precise resolution devices to reject signal from this second source. This second ideal wave would be rejected by the focus operation using uncorrected signals, but a second set of distortion waves that it engenders would not. It is necessary to reject this second set of distortion waves so as to reject any signal that comes from the second source. Measurement of distortion waves is still done with forward propagation, but the presence of the second ideal wave complicates the process. An efficient way to control the second ideal wave, is to continue the forward propagation process where a focusing device is inserted to focus ideal waves to small spots of high intensity. The distortion waves would be flattened in the process. The flat distortion waves would be sensed by a flat transducer, which would be steered to locate sources of distortion waves, and thus locate corresponding signal points where corrections would be applied. The focused ideal waves would be subjected to a process, such as clipping in the electronic circuits, so that their intensity would be greatly reduced and their impact on measurement of distortion waves would be minimal.

Multiple undesired sources would be handled in this manner.

The flat distortion waves could alternatively be sensed using optical scanning, as done in acoustic holography. Such optical sensing offers a very efficient beamforming process. The continuation of the forward propagation process could alternatively be established by an additional receiver array and relay transmitter array. A subtraction technique could also be used to contend with the multiple sources, where signals from the first receiver would be beamformed to measure the set of unwanted sources to determine an approximate correction which would minimize affects of these unwanted sources.

DETAILED DESCRIPTION OF THE PREFERRED EMBODIMENTS

Figure 2:
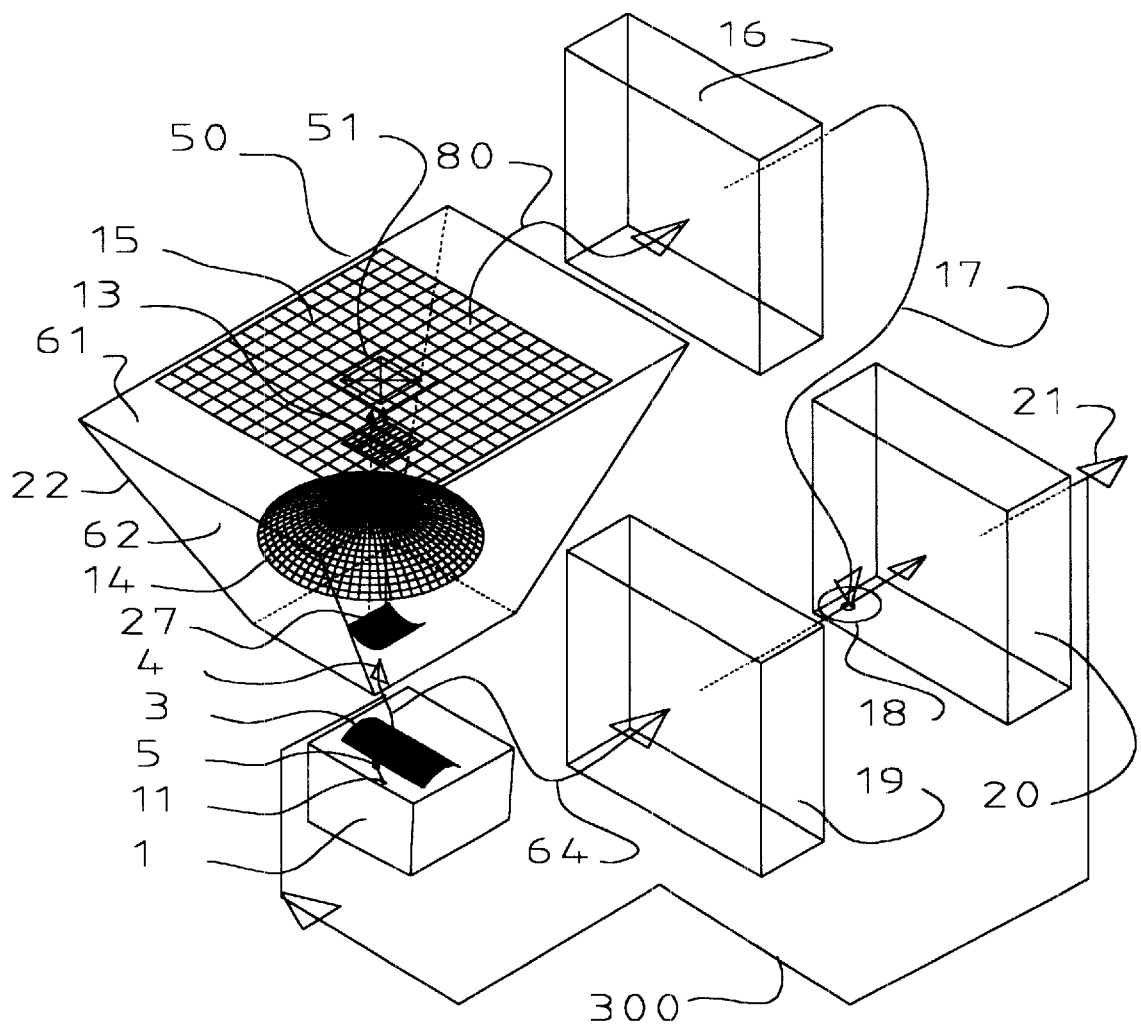
FIG. 2 is a diagram that illustrates a basic embodiment of the present invention using a combination diagram that depicts wavefronts using wire mesh graphics along with physical depictions of physical system equipment and block diagrams of computational system equipment.

FIG. 2 illustrates a basic configuration that is an embodiment of the present invention. It shows a source 11 of a wave in a medium 1. An irregularity 5 makes the medium inhomogeneous. The irregularity 5 has an effect on the wave that is equivalent to an ideal wave and a distortion wave. This represents multiple distortion waves that may be refraction distortion waves or diffraction distortion waves, to be discussed later. The representative distortion wave propagates to a first aperture that is established by a first receiving device 3. The first receiving device 3 samples the waves over the first aperture to create original received signals 4. Original received signals are transmitted by a relay transmitter array 27 to establish forward propagation. Points on the first receiving device 3 are in one to one correspondence with points on the relay transmitter array 27 with appropriate signal conditioning to convert a spherical ideal wave at the original receiving aperture next to the first receiving device 3 to a plane wave that emerges from the relay transmitter array 27. Thus forward propagation of a collimated form of the ideal wave 13 and a spherical form of the distortion wave 14 occurs in a clear medium 61 in a container 22. Container walls are lined with absorber 62. An ultrasonic implementation would utilize a low attenuation medium 61 such as water. As forward propagation occurs, the spherical distortion wave 14 becomes increasingly spread out relative to the collimated ideal wave 13 and a second receiving device 15 senses both. The second receiving device 15 utilizes selective sensitivity of a beamformiing process 16 to measure the spherical distortion wave 14 at the measurement plane 50. Measurement of distortion waves extracts amplitude and timing for waves that are attributable to small regions on the aperture of the relay transducer. An ignore zone 51 is a region where the distortion measurement process ignores signals, which means setting values in a data set to zero. The ignore zone is approximately a projection of the planar version of the ideal wave 13. Corrections 17 are determined for sampled points on a plane near the relay transmitter array 3. Corrections for these sample points are applied to respective receive signals. The determined corrections 17 are applied 18 to duplicates 64 of the original received signals that are held in memory 19 while the forward propagation process takes place. The corrected signals are then summed in a final beamforming process 20 that focuses on the original source of the wave and output signals 21 are produced. In the illustration, only output signals 21 represents only one signal data point which corresponds to the one source point 11. Provisions for electronic scanning to view other source points are understood to be part of the embodiment, but are not shown. Iteration 300 is a further way to enhance reception.

Figure 3:
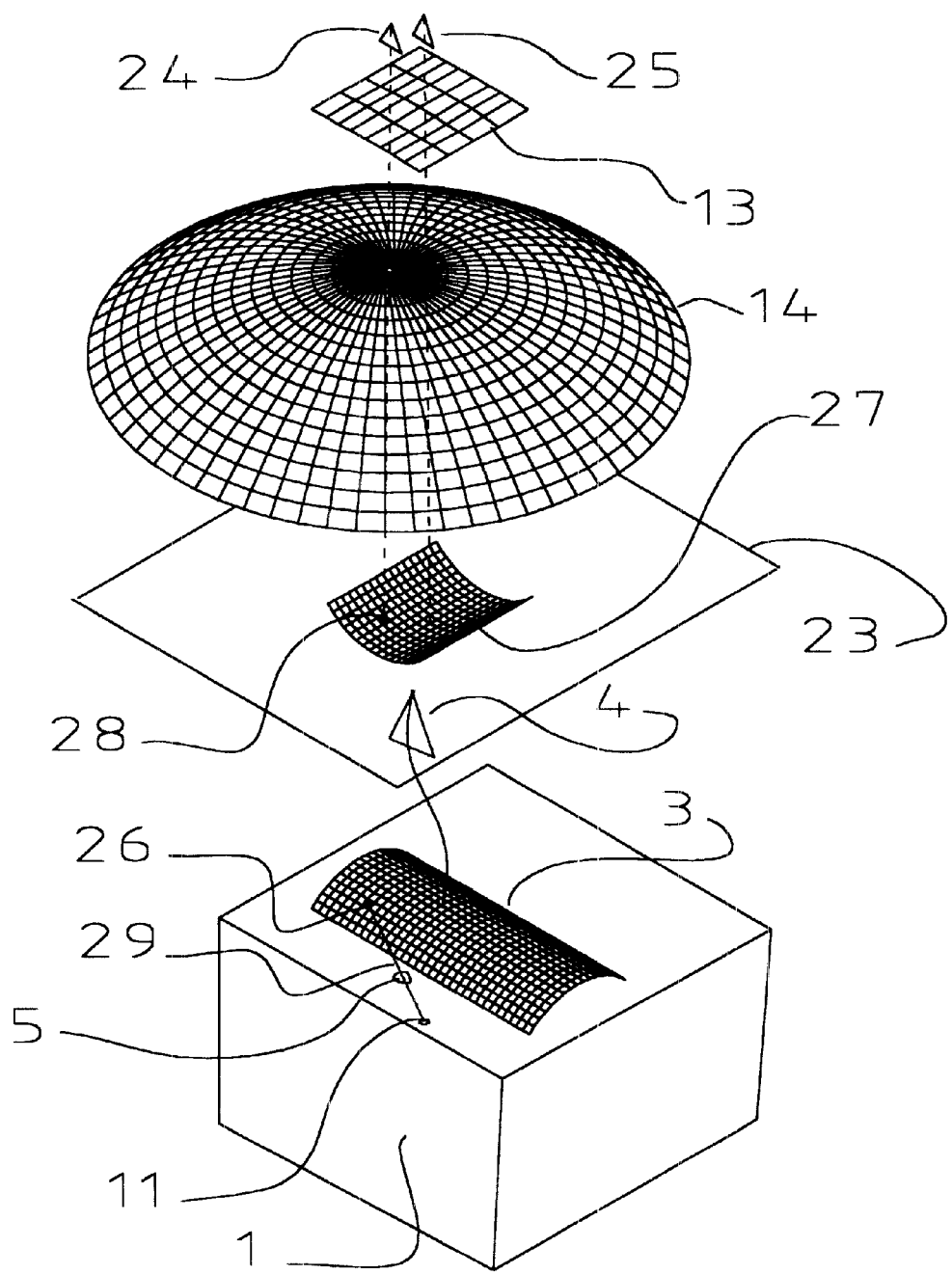
FIG. 3 is an expanded view of parts of FIG. 2 to show wavefronts in relation to transducer grid configurations.

FIG. 3 shows more detail of the propagation processes including a container bottom 23. Signal from the origin 11 travels through the uniform medium 1 along a path 29 to encounter the irregularity 5. A distortion effect 26 is indicated at the first receiving surface 3 and its transfer 28 to a relay transmitter is also indicated 27. Here can be seen a better view of the collimated wave 13 which is the carried forward version of the ideal wave that was initially received. The path 24 of the distortion wave and the path 25 of the collimated wave are indicated by dashed lines with arrowheads. Receiver surfaces for the original receiver array 3, the relay transducer array 28, and the measurement receiver array 15 are shown with the actual transducer element divisions as lines on the drawing. The forward propagation distance along paths 24,25 is substantially greater than propagation distance along path 29. This allows spherical spreading of the distortion wave from its carried forward origin 28 where it is still similar in size to the relatively large irregularity 5. For small irregularities the carried forward distortion wave origin 28 can be significantly spread to distribute itself over the relayed aperture of relayed transducer 27. This has the effect of causing multiple spherical waves which are only represented by the single spherical wave 14. The ultimate need to cancel detailed irregularities drives granularity of the original receiving transducer 3 and the relay transducer 27, meaning the element size and spacing details.

Measuring and suppressing the distortion waves as discussed above requires equipment that was designed using general principles of ultrasonic devices. Array technology from that field is applicable and the sources of such component devices are likewise sources of properly developed equipment for the present invention. Transducers shown in FIG. 2 and FIG. 3 are two dimensional surfaces that are constructed using piezo-electric materials that are divided into elements using a dicing saw, where such dicing saws are common in the semi-conductor industry. Figures depicting transducers show only surfaces of the transducers with lines indicating saw lines that divide elements. Additional cuts are made to sub-divide elements but these are not realistic to show in the drawings that are the accompanying figures. Ultrasonic transducer companies provide the necessary expertise to produce the specific configurations needed here.

Consistent with the ultrasound field and the sonar field, the term beamforming is used to mean a process of measuring wave signals by taking signal samples over an aperture, adjusting them in time for an assumed point source, and adding coherently. Beamforming is generally effective for excluding signals from all locations except the assumed point, so it can specifically measure distortion waves. A lens focuses signals to accomplish the same purpose though a typical lens beamforms for many assumed points in parallel, thus forming an image from an object. Electronic beamforming is also capable of forming many receive beams in parallel by repeatedly processing a set of signal samples using different time adjustments.

Parallel beamforming is important in the preferred embodiment and in alternatives because a beam must be formed for each of the many points from which distortion waves might emerge from the plane near the relay transducer 27. Noting that there is an approximate one to one correspondence between points on the plane near the relay transducer 27 and received signals, each respective beam is a signal that becomes a correction signal to be applied to respective signals from the receiver. Such signals from the receiver must be held available in memory 19 while the corrections are being determined. Applying corrections 18 is a coherent subtraction process that is carried out prior to the final summation that focuses on the origin of the ideal wave. Coherent subtraction means that phase or timing of signals must be properly aligned. Such alignment requires precise calibration of system timing by artificially inserting test signals.

The same process can be implemented with lens devices rather than electronic beamforming. Lenses are known in ultrasonics as well as optics. However, with a lens implementation, the duplicate received signals must be extracted and a delay process is necessary where the duplicate received signals are made available for correction during the forward propagation time.

Figure 1:
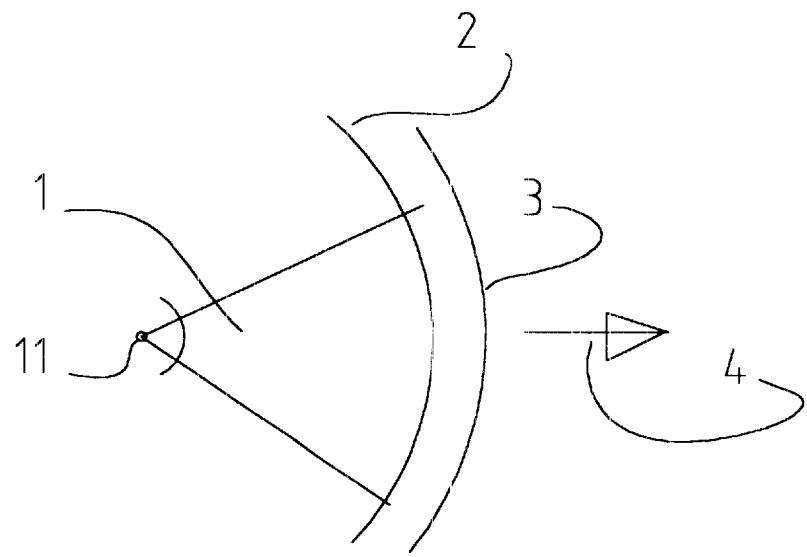
FIG. 1 (prior art) compares an ideal wave in a homogeneous medium with a wave in a medium that contains a wave speed irregularity and a blockage.
Figure 1:
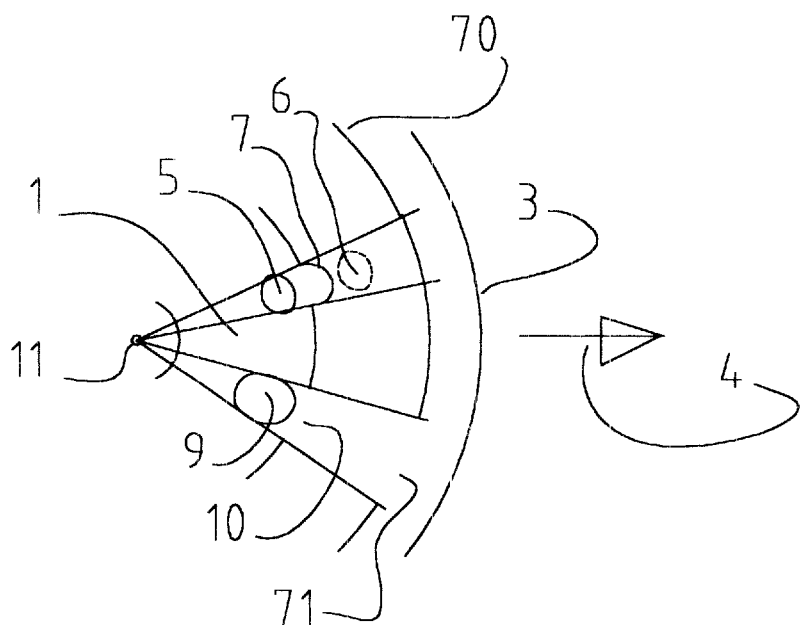

To understand the operation of this device requires understanding of the basic approach of this invention as contrasted with a common approach. FIG. 1(a) illustrates an idealized wave process in a clear medium 1 where a wave travels from a source 11 to a receiving aperture 3 that is established by a receiving device which produces received signals 4. The ideal wave is undisturbed so it is represented as an ideal wavefront 2 as it arrives at the receiving aperture 3. FIG. 1(b) illustrates simple aberration conditions and a correction which represents the intended function often attempted by aberration correction technology. The same point source 11 produces a wave which encounters a localized material 5 having a different wave speed than the general medium 1. The wave also encounters a blockage 9. The resulting wave is shown as a wavefront with a bump 7 and a gap 10. As discussed under prior art, the common concept of correction is idealistically represented by a counter lump 6, which reverses the sound speed variations of localized material 5 to restore that part of the ideal wave immediately after it is caused. There are two problems that are not effectively solved by such attempted technology. First, the idealized effect of the correcting counter lump 6 can not be acceptably approximated by electronic processes, where these electronic processes are applied after propagation of the distorted wave over an unknowable distance to the receiving aperture 3. Second, correcting the gap 10 by time adjustments is not meaningful so the ultimate wave 70 continues to include a gap 71. These are the problems that are addressed by the present invention.

The new approach revives and extends a traditional method of formulating wave distortion problems. This traditional method defines effects of objects in the path of a wave as an incident wave and scattered waves. The incident wave is the wave that would have continued if the objects were not present, in other words, an ideal wave. Scattered waves are the waves that must be added to the incident wave to produce the actual physical situation. This terminology is very misleading, yet it has survived since Rayleigh and before. It appears to be based on Babinet's Principle in optics.

A presumption is that there is a uniform medium that contains irregularities. For limited types of medium imperfection, such as where wave speed varies slowly over a relatively large spatial extent, it is possible to artificially establish conditions that approximately satisfy this criterion. This is done by applying slowly varying corrections to time of arrival.

The present premise is that distortions result a wave field that is equivalent to a summation of an ideal wave and distortion waves. If the distortion waves can be cancelled, then the ideal wave will remain. This is rooted in Babinet's principle, which guides us to a transformation that provides an equivalent to an actual wave field. In the traditional formulation of scattering problems, the equivalent is found by decomposing the actual wave field into the idealized incident wave and the scattered wave fields. After these components are separately analyzed, they are summed to describe the actual field. Here the term "scattered wave" is replaced by the term "distortion wave" and the term "incident wave" is replaced by the term "ideal wave."

Figure 4:
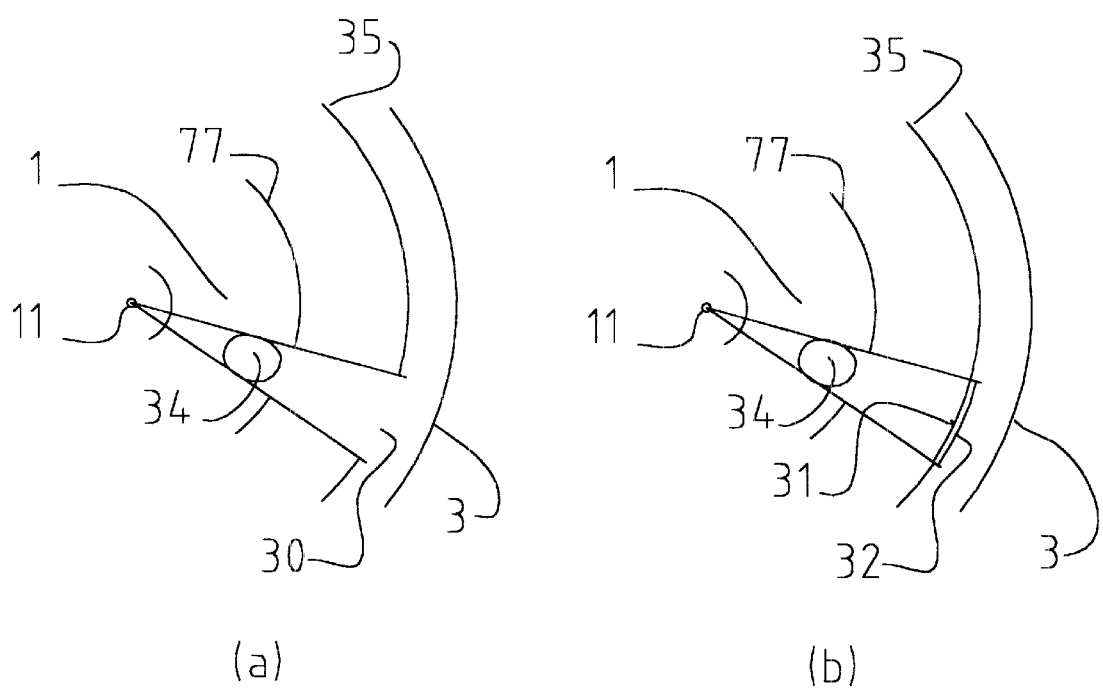
FIG. 4 illustrates an interrupted wave and its decomposition into an ideal wave and a distortion wave, where a summation of components is equivalent to the interrupted wave.

FIG. 4 helps to envision and analyze the mechanism by which diffraction occurs. FIG. 4(a) schematically indicates a blockage condition 34 and the ensuing distorted wave 77 and its projection 35 that would contain a gap 30. FIG. 4(b) shows the the equivalent to the distorted wave 35 that is a combination that original wave 35, a patch 31 to make it the same as an ideal wave, and a new part 32 that keeps the patch from changing the physical situation. It is elementary math that if a patch is added and an exact negative of that patch is also added, then nothing has been done to the physical situation, as required. Here the negative of the patch is called the patch-negative wave. A correct portrayal of a patch 31 and a patch-negative 32 would require two lines superimposed, but they are shown here only approximately superimposed. Lines do not enable indicating that one is exactly the negative of the other. The patch-negative wave is a distortion wave that is a diffraction wave. There are now two waves to consider that are the ideal wave and the patch-negative wave, both of which will propagate according to simple rules. Addition of the two will exactly produce the original condition, but if such addition is done after propagation it is possible to understand wave processes that would otherwise require computer analysis. In some directions the ideal wave will vanish and the only significant part left is the patch-negative wave. This is the condition observed by Babinet. This representation shows how the diffraction process heals the actual wave. When both parts propagate far enough, the patch-negative wave will become much like the ideal wave and addition of the two will result in a smooth wave that is simply reduced in amplitude. The apparatus of FIG. 2 is constructed on the basis of this analysis method. Propagation to the initial receiver is first analyzed. Then the forward propagation apparatus is constructed such that the patch-negative wave and the ideal waves undergo propagation processes that cause them to be in a form that allows separate measurement of the patch-negative wave.

Figure 5:
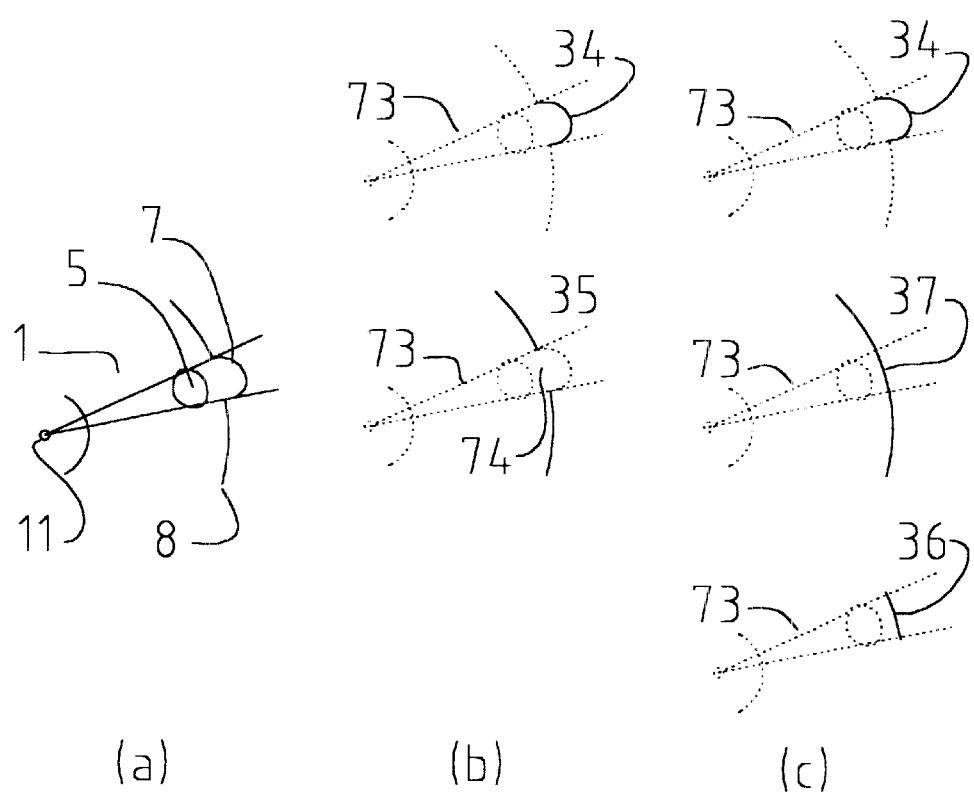
FIG. 5 illustrates decomposition of a physical wave that encounters a wave speed irregularity and a blockage, where a summation of the components is equivalent to the physical wave.

FIG. 5 examines a more complicated situation. In this case a transformation to an equivalent situation is carried immediately after the localized disturbance 5. As shown in FIG. 5(a), unlike a simple blockage condition, this localized wave speed variation 5 results in a distorted form 8 that includes a bump 7. FIG. 5(b) shows decomposing this distorted condition into a small bump wave 34 and unaffected sections 35 of the intended wave. Dotted lines in this figure enable registration of comparisons between figure parts (a), (b), (c). The small bump wave 34 has a wavefront shape that is determined by the wave speed variation effect. This is a refraction distortion wave 34. FIG. 5(c) shows how another wave is created by the gap 74, according to the rules previously developed in reference to FIG. 4 for a blockage caused gap 35. Like before, this gap also leads to an ideal wave and a patch-negative wave, where the latter is again a diffraction distortion wave 36. This diffraction distortion wave is a result of something being removed from the ideal wave leaving a gap in the ideal wave. Thus, refraction results in both a refraction wave 34 and a diffraction wave 37, as well as an ideal wave 37. It is valid to study forward propagation of these three component waves 34,36,37 and then combine the results that come about at a later time, after propagation.

A reflecting object may cause a blockage that results primarily in a diffraction wave. It may also cause a reflection distortion wave. Localized variations in attenuation cause partial blockage that primarily produces a diffraction effect.

Compared to prior art in ultrasonics, it appears that finding the diffraction wave as a product of refraction is a significant discovery. It is made more significant with the realization that diffraction waves caused by all localized refraction and reflection conditions and by localized blockages are all in mutual phase relationship, such that significant degradation can be attributed to this effect.

Although it might seem that refraction simply causes a bump on the wavefront, this discussion has shown this is not the case. Of course, if the bump were immediately reversed, as discussed in FIG. 1, then a diffraction condition would not be established. If the reversal is not immediate, it is clear that a very complicated situation would exist.

An actual situation might involve many refractive conditions and blockages as well. Aberration problems caused by a set of all patch-negative waves can be especially severe. Because they are all mutually in phase such they tend to add more effectively than more random refraction waves. This discovery is a satisfying explanation of the structure that is observed in response functions of ultrasonic beamforming systems where the propagation medium is human tissue. It also explains disappointing results for development projects that would correct for aberrations by time adjustments that were applied for waves that had propagated from the point of disturbance.

This formulation of the effects of diffraction then leads to a new approach in aberration correction. Rather than attempting to repair the ideal wave by adjusting timing of received signals, the present invention repairs the ideal wave by measuring and subtracting the distortion waves. This approach is applicable to a variety of sizes and types of irregularities.

A major issue is the off-bean response issue, where signals come from multiple original points. This means that the ideal wave becomes multiple ideal waves. An effective receiver can exclude all ideal waves except for the intended ideal wave, but it is much less able to exclude distortion waves that arise from unintended ideal waves. It is possible in some environments that severe off-beam response is thus caused by the distortion waves. The basic apparatus of FIG. 2 senses all such distortion waves. However, the presence of many ideal waves reduces accuracy of measurement of these distortion waves.

Figure 6:
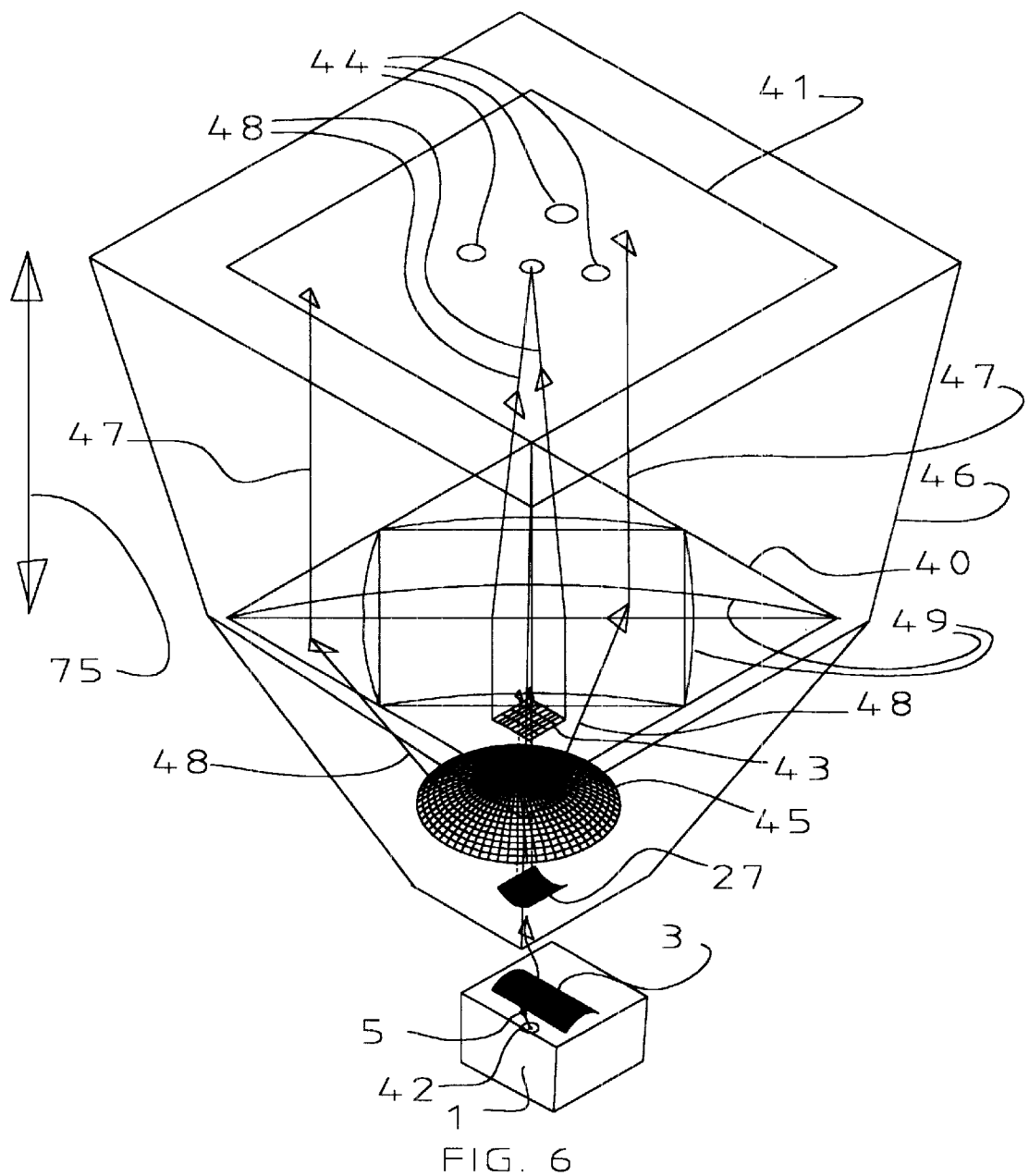
FIG. 6 illustrates an extension of the basic invention to improve measurement of a distortion wave by concentrating an ideal wave. It also indicates a plurality of wave sources which would operate to create a plurality of ideal waves not shown and a plurality of concentrated ideal waves.

FIG. 6 illustrates an expanded form of the basic invention where additional measures are taken to minimize the impact of ideal waves on the process of measuring distortion waves. While the principles of the invention are applicable to any type of wave, and forward propagation can be a different type of wave from the basic sensing method, this is an alternative embodiment that is an ultrasonic application, both for the basic sensing and the forward propagation process. modification of the forward propagation process is arranged by a refractive device that causes the collimated ideal waves to be focused at points and the distortion waves to be approximately collimated.

All waves are sensed as before, but the high intensity focus points are clipped in amplitude to minimize their contribution to the second beamformiing summation that measures the distortion waves. For ultrasonic wave receiving equipment, distortion wave measurement utilizes ultrasonic transducers using adaptations of medical ultrasound transducer technology. The wave forms are also suited to measurement by optical technology as now used in the field of acoustic holography.

FIG. 6 illustrates a uniform medium 1 with a cluster of sources 42, one of which is an intended source that has a path 5 to an original receiver device 3. Signals transfer to a relay transmitter 27 that is shaped to indicate a combination of signal processing and receiver shaping such that a wave 43 from the intended source would be centered and would travel vertically in the system as shown. Waves from other sources in the cluster 42 would be collimated plane waves as is the central wave 43, except they would travel at angles off vertical. The previous tank would be extended 46 with absorber lined walls. Distortion waves 48 would also emerge from the relay transducer 27. An ultrasonic lens 40 is inserted such that it lies along a plane perpendicular to the vertical axis. This lens is constructed with ribs 49 over which is stretched Mylar film to form a container which contains a fluid that provides refraction as with a lens. Though alternates are concave, the convex form shown requires a fluid having ultrasonic wave speed that is slower than water which is the general medium in the forward propagation tank. Ethyl alcohol is a selected material for this embodiment of the lens to give nearly ideal coupling with the water yet providing a refractive index that is adequate. An additional forward propagation distance 75 is set so that plane waves at the lens are focused to a minimum size at the measurement plane 41 as depicted by rays 48 that converge. The presence of undesirable sources in the cluster 42 gives rise to focus points 44 at variable locations. These are concentrations of energy that are to be minimized, and this is done by signal clipping. An alternate method is to allow computer processing to search for peaks and zero out signals in the related vicinity. Distortion waves are converted to plane waves as representatively indicated by parallel rays 47. The measurement plane 41 is established by a transducer array where signals are produced which are collected by the beamforming equipment. Beamforming is simplified by the plane waves that are to be searched for, and for narrow band alternative embodiments, FFT methods are especially efficient. The present embodiment uses time sample beamforming where time delays are provided by a parallel shift register arrangement with summation as is well known in sonar as digital multi-beam steering (DIMUS).

Figure 7:
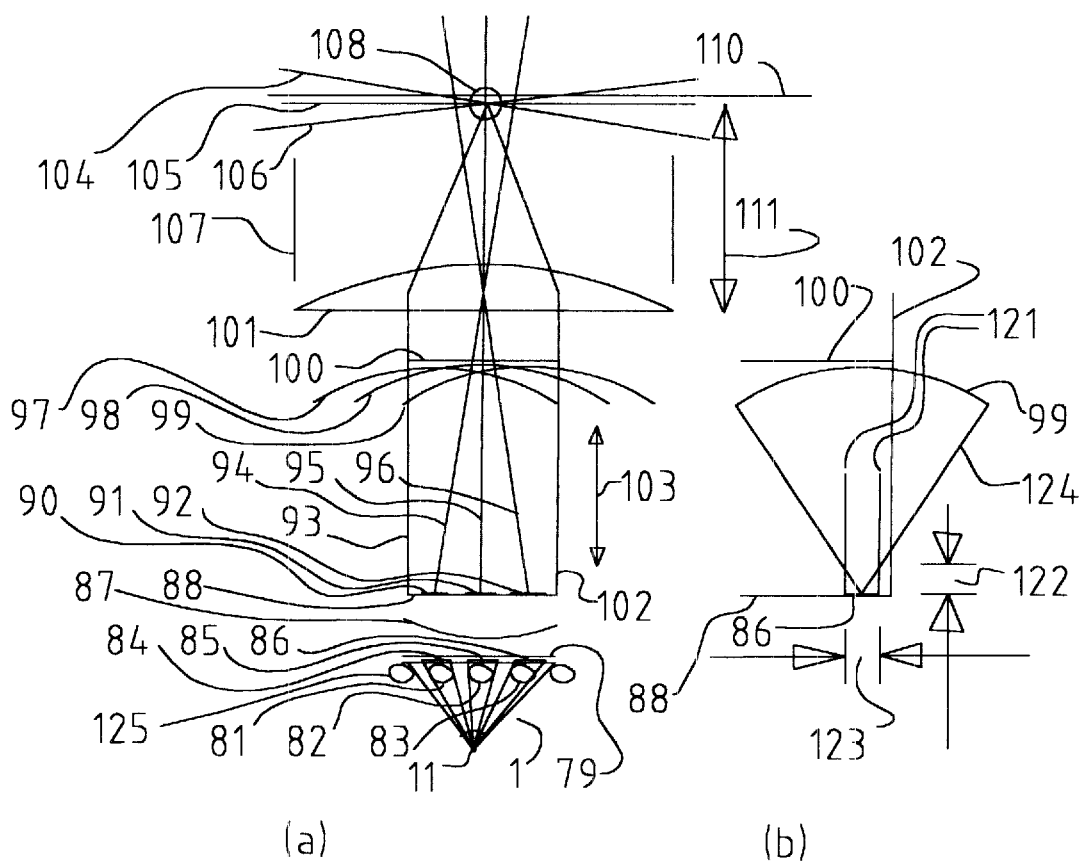
FIG. 7 illustrates a one dimensional line array in a conventional ultrasound system with one dimensional transducers in an apparatus to suppress distortion waves according to principles of the invention. It also further illustrates basic principles of the invention using a less complicated two dimensional presentation.

A major breakthrough in ultrasonic breast imaging is possible as a result of the present invention. Other ultrasonic applications are being examined; cardiac imaging through the rib cage is another area for possible application of this method. FIG. 7 illustrates a cardiac imaging version that is attached to a large line array 79 built according to the general architecture of conventional ultrasound systems. The forward propagation equipment would involve a line array as the relay array and a line array as the second receiver that would measure distortion waves. In this configuration it is possible to expedite the signal processing since some advanced knowledge of the position of blocking ribs would be available to operators. This would be useful in limiting the amount of searching for distortion waves by the distortion wave measurement process. Note however, that this line array configuration has a fundamental limitation in controlling elevation angle and the aberration correction would not help with that and it would also not eliminate aberration effects that occurred in this same elevation dimension.

FIG. 7(a) illustrates the details of this apparatus and FIG. 7(b) illustrates spatial relationships that apply in this case as well as in general. A source point 11 in a clear medium 1 emits wave signals that are partially obstructed by ribs 81,82,83 that are obstructions within the aperture of the receiver 79. An outer rib 125 in the illustration partially blocks the aperture but it serves to slightly shorten the effective aperture, which is a condition beyond reach of correction. Rib positions are approximately measureable by the operator relative to the line array receiver 79. A relay transmitter 87 signifies a combination of signal processing and shaping by which a plane wave 87 is produced which is associated with the intended source 11. Distortion waves 90,91,92 are approximately originating at the location shown and these become spherical waves 97,98,99 respectively. Lens 101, built according to instructions for that lens for the previous figure, focuses the plane wave from the intended source in a region 108 that is small compared to the extent of plane waves 104,105,106 that are due to respective ribs 81,82,83. Signal measurements are taken at measurement plane 110 by a linear array receiver that is parallel to that measurement plane, but not shown. Distance of forward propagation 103 and its extension 111 are designed in conjunction with the lens and guidance given in FIG. 7(b). FIG. 7(b) illustrates a single patch-negative 86 that is due to blockage by the rib 83. The ideal wave 88 is also shown here. The dimension 123 and the wavelength determine spreading angle indicated by an angled line 124 to give the spherical wave 99 as shown. A vertical dimension 122 indicates the transition from collimated condition indicated by vertical lines 121 to the far field spreading condition. At the same time the ideal wave 88 carries forward in propagation as a collimated system to produce a later wavefront 100. The collimated condition for the ideal wave is indicated by the vertical line 102. The ideal wave transitions to a spreading condition at a much greater distance than the patch-negative wave 86 transitions to a spreading condition. These relationships determine design details of this embodiment, and the same principles apply to the other embodiments as well.

Previous discussion has mostly assumed that beamforming is the primary process for measuring the distortion waves. However, FIG. 7(b) depicts time separation of a distortion wavefront 99 from an ideal wavefront 100 that enables time gating to isolate sections of the distortion wavefront that improves beamforming where strong ideal waves are present.

Optical imaging devices may encounter similar difficulties with propagation, which can be fixed by this invention. Optical processing devices provide equivalents to corresponding ultrasonic processing devices that have been described. The very wide field of this invention also includes many applications that will become apparent from the descriptions of the basic method of the invention as well as embodiments that are examples. However, the claims that follow this specification determine the scope of the invention.

Holography, including acoustic holography, is a system that beamforms using coherent optical methods. It determines distortion waves and uses this information to generate an image of a medium. Holographic imaging does not require measurement of the ideal illuminating wave, which is a fixed and pre-determined wave field and not an object to be sensed. In the present invention the intention is to carry out a similar process, except the distortion waves are subtracted to leave only the ideal illuminating wave, which is not pre-determined, rather, it is the object to be sensed. Holographic technology provides a way to measure distortion waves for purposes of determining the distortion wave information to subtract, as is the purpose of the present invention. An alternative to the beamforming described in connection with FIG. 6 is the use of optical scanning to sense to plane distortion waves as formed in this apparatus.

The present invention has been described as a device to receive signals from a single point. It must be understood that in medical imaging, the present invention requires receiving and restoring many such ideal waves in order to generate an image that shows a reasonable field of view. For each wave source, delays would be applied to the original received signals to cause the forward propagation to be appropriately directed for a given wave source point and the final summation beamforming process would also be appropriately focused on that source point. The most common use of this device is expected to be ultrasonic imaging where additional capabilities such as transmitting of signals and display of signals would be included, according to basic principles of medical imaging devices. The same principles would be applicable in detailed design of the forward propagation parts of this device and the computational processes that are uniquely required for subtraction of distortion wave signals.

There are many possible variations in design of the system. System designers will apply guidance in this disclosure to implement specific equipment in their respective fields. Devices specified here will be made to fit by analysis of respective designs, where that analysis enables appropriate scaling to necessary dimensions with appropriate timing and appropriate numbers of channels. The forward propagation medium may not be the same as the original wave medium. Transducers shown are piezo-electric devices that are adapted from ultrasonic medical imaging technology, but other devices provide equivalent functions. For example, optical systems are possible where lenses are used establish forward propagation while a variety of optical devices are used to arrange sufficient delay of original received signals so that the distortion signals can be subtracted.

Figure 8:
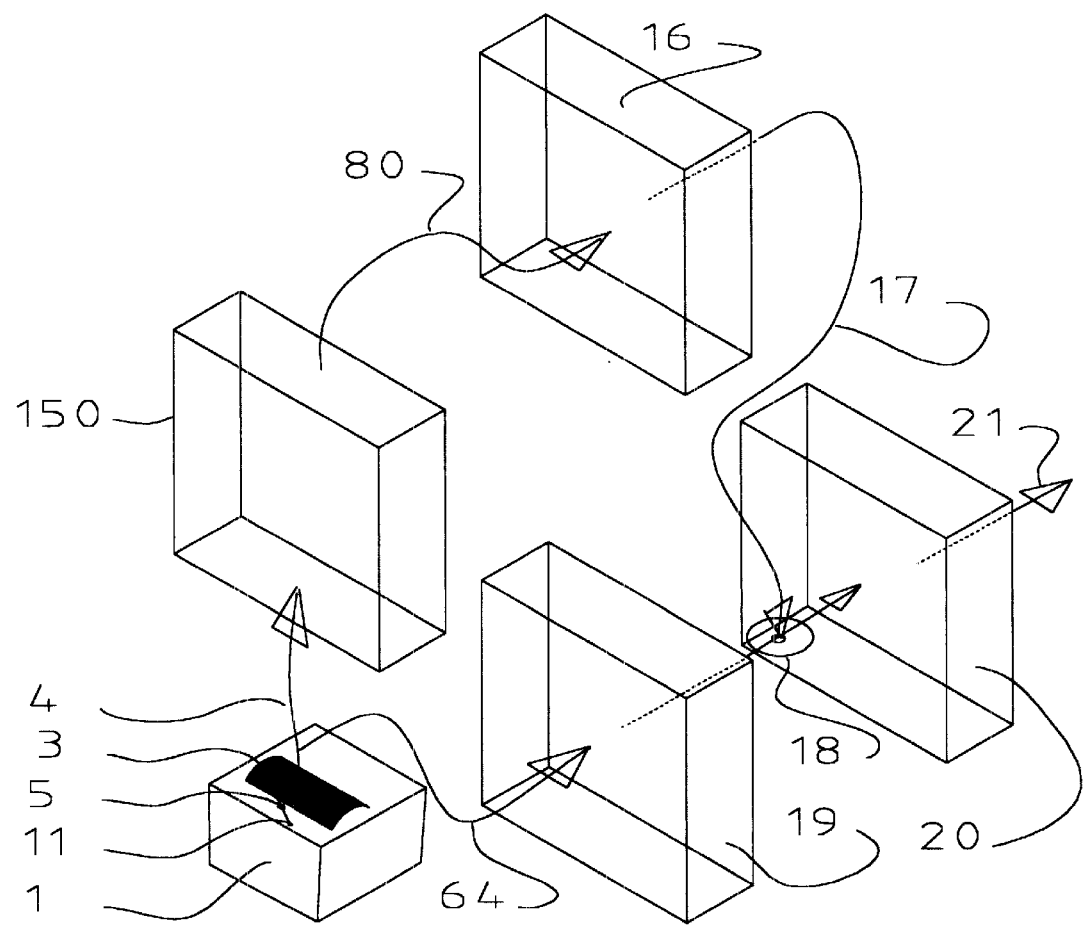
FIG. 8 illustrates a computational equivalent of forward propagation in a system according to principles of the invention.

FIG. 8 indicates a computational equivalent 150 to the forward propagation process of FIG. 2 that is inserted in replacement of the relay transducer, the tank, and the receiving transducer. The effect of wave propagation is here derived from the received signals and the wave at an appropriately distance to produce the spreading of distortion waves would be computationally determined. The equivalent of the ignore zone would be imposed by computer logic processes. A similar computational equivalent would be based on the variation of FIG. 6. Computational equivalents to the forward propagation process require a summation, for every point sample at the virtual measurement that plane, of all sample points on the virtual relay transmitter surface. The resulting measurement plane signals 80 would be subjected to beamforming 16 as discussed for the basic system of FIG. 2.

Although there is no restriction to any of the many fields where this invention would be applicable, seismic prospecting may be a field particularly open to use of such computational variations since off-line processing is the usual mode of operation.

Figure 9:
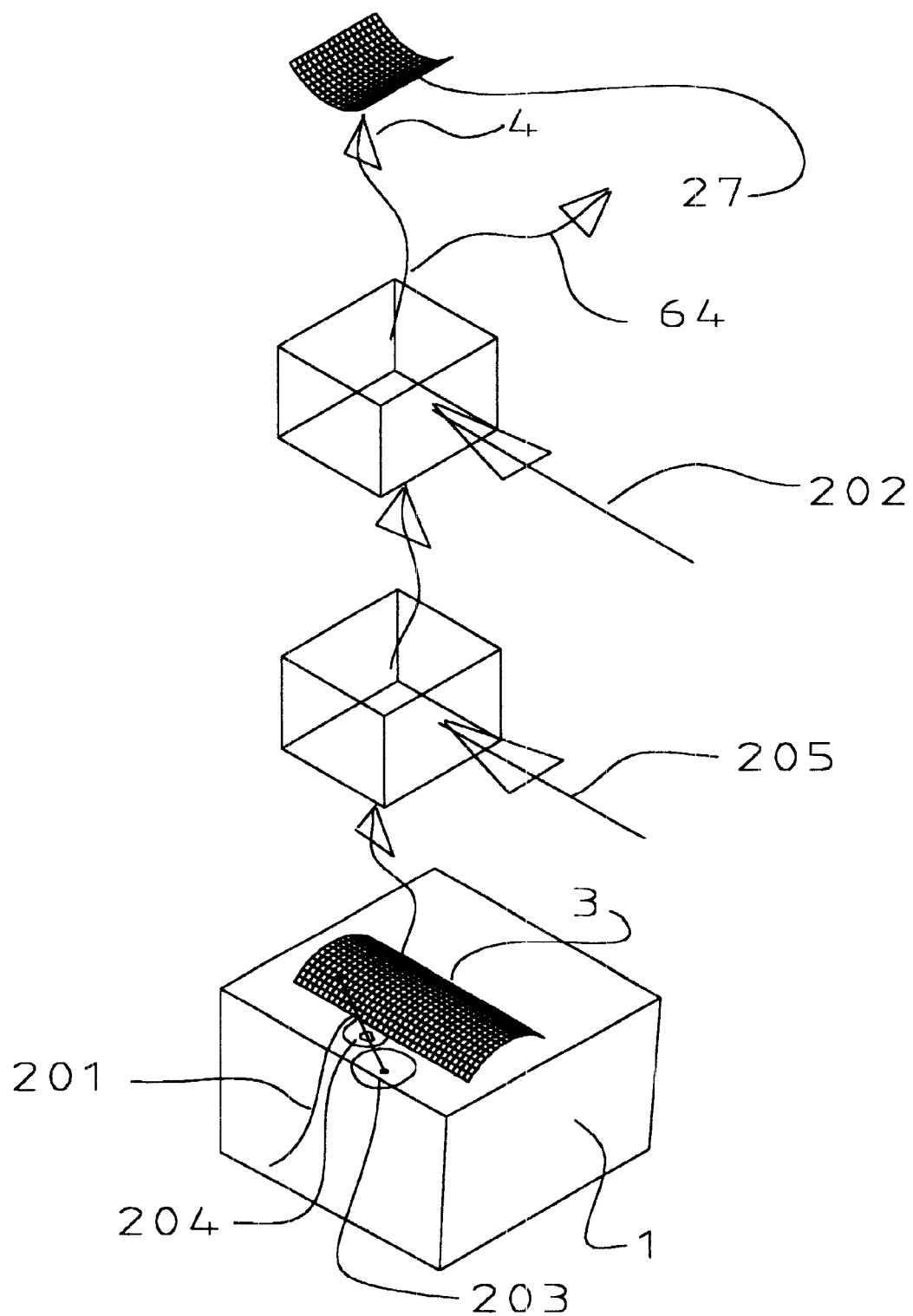
FIG. 9 illustrates integration of the invention into an ultrasonic medical imaging system.

FIG. 9 illustrates integration of the invention into an ultrasonic medical imaging system scanning a breast 201 This involves insertion of transmit signals 202 that are compensated for frequency dependent attenuation. A fairing arrangement enables scanning and attenuation leveling makes compensated transmit signals valid over the fill aperture. A switch enables transmit and receive operation with the same transducer. Scanning capability is also indicated for the illustrated cylindrical array form 3, where such scanning is electronically carried out laterally along the axis of the cylinder. Mechanical translation scans this axis throughout a volume. Multiple objects 203 are to, be sensed to form an image. Multiple irregularities 204 are also shown. A process of applying general wave speed corrections 205 to both transmit and receive signals is also shown.

Thus a variety of devices have been discussed that are embodiments of the fundamental concept of the invention that is a unique approach to aberration correction. This concept is to sense and subtract distortion waves, rather than compensating for timing errors caused by speed variations in a medium, and is thus a significantly different approach.

What is claimed is:

1. An apparatus to enhance wave reception comprising:

a source and a receiver, where an intended wave propagates from said source to said receiver in an inhomogeneous medium, where said receiver produces received signals, and where said inhomogeneous medium is an approximately homogeneous medium contains an irregularity that is localized, and said irregularity causes said intended wave to be a distorted wave that is equivalent to a summation of an ideal wave and a distortion wave, where said ideal wave is equal to said intended wave had there been no said irregularity, and a forward propagation relay device that causes continued propagation of said distorted wave by secondary transmission of said received signals, and said continued propagation takes place in an approximately homogenous medium, where said continued propagation of said ideal wave and said continued propagation of said distortion wave results in a continued ideal wave and a continued distortion wave respectively, and said forward propagation device enables selective measurement 'f said distortion wave, and a device to sense and measure said continued distortion wave, and a device to determine correction signals from measurement results, and a device to retain replicas of said signals from said receiver, and a device to apply said correction signals to said replicas to suppress effects of said distortion wave, and a device to produce an output signal that is approximately not affected by said irregularity.

2. An apparatus according to claim 1 where said continued propagation is modified by a focusing device to minimize an effect of said ideal wave on accuracy of measurement of said distortion wave.

3. An apparatus according to claim 1 that implements said forward propagation relay device with a computational process that is equivalent to said forward propagation relay device.

4. An apparatus according to claim 1 that implements a combination of said forward propagation relay device and a focusing device to minimize an effect of said ideal wave on accuracy of measurement of said distortion wave using a computational process that is equivalent to said combination.

5. An apparatus according to claim 1 where said source is a plurality of sources, and one of said plurality of sources is an intended source and said distortion wave is a plurality of distortion waves.

6. An apparatus according to claim 1 where said irregularity is a plurality of irregularities and said distortion wave is a plurality of distortion waves.

7. An apparatus according to claim 1 where said distortion wave is a plurality of distortion waves.

8. An apparatus according to claim 1 where said distortion wave is a diffraction distortion wave.

9. An apparatus according to claim 1 where said distortion wave is a refraction distortion wave and a diffraction distortion wave.

10. An apparatus according to claim 1 that is a part of an imaging system.

11. An apparatus according to claim 1 that is a part of a detection system.

12. An apparatus according to claim 1 that is an ultrasonic system.

13. An apparatus according to claim 1 that is a part of a seismic system.

14. An apparatus according to claim 1 that is a part of a sonar system.

15. An apparatus according to claim 1 that is a pert of a radar system.

16. An apparatus according to claim 1 that is apart of a communication system.

17. An apparatus according to claim 1 that is part of an industrial inspection system.

18. An apparatus to enhance reception in an optical apparatus where optical receiving is enhanced with optical devices that carry out functions that correspond to and are approximately equivalent to functions of an apparatus according to claim 1.

19. An apparatus according to claim 1 where said irregularity is a local variation in wave speed that causes both a diffraction distortion wave and a refraction distortion wave.

20. An apparatus according to claim 1 where said irregularity is a local variation in attenuation of said medium.

21. An apparatus according to claim 1 where said irregularity is a local discontinuity of impedance of said medium.

22. An apparatus according to claim 1 where said irregularity is a local variation that causes both a diffraction distortion wave and a reflection distortion wave.

23. An apparatus according to claim 1 and attenuation leveling to cause wavefronts of constant amplitude over a surface of said wavefronts.

24. An apparatus according to claim 1 and signals that are compensated for frequency dependent attenuation.

25. A receiving system according to claim 1 where said receiver is synthesized by a small receiver that is moved to successive positions while said signal is correspondingly repeated, and signal processing to produce large receiver effects.

26. An ultrasound receiving system for receiving a signal from a source in a medium, comprising:
   a signal source which causes propagation of a wave through said medium, where said wave is distorted by a distorting object in said medium to cause a distorted wave, and said distorted wave is equivalent to an ideal wave and a distortion wave, where said ideal wave is an undistorted form of said wave, and where said undistorted form is equal to said wave as if said medium contained no distorting objects, and
   a wave receiver device which receives said ideal wave and said distortion wave at a receiving aperture to produce received signals, and
   a device to process said distortion wave to determine correction signals, and
   a device to retain signal replicas of said received signals, and
   a device to apply said correction signals to said signal replicas to suppress effects of said distortion wave, and
   a device to process corrected signals to produce an output signal.

27. A computer simulation of a receiving system according to claim 26.

28. A receiving system according to claim 26 where said receiver is synthesized by a small receiver that is moved to successive positions while said signal is correspondingly repeated, and signal processing to produce large receiver effects.

29. An ultrasonic receiving system according to claim 26 where said source is a plurality of sources, and one of said plurality of sources is an intended source.

30. An imaging system for obtaining a high resolution, high contrast image of image objects in a medium, comprising:
   a wave source which transmits a wave through said medium to cause reflections from said image objects to produce reflected waves, where said reflected waves are distorted by distorting objects in said medium to cause distorted waves, and said distorted waves are equivalent to ideal waves and distortion waves, where said ideal waves are undistorted forms of said reflected waves, and where said undistorted forms are equal to said reflected waves as if said medium contained no said distorting objects, and
   a wave receiver which receives said ideal waves and said distortion waves at a receiving aperture to produce received signals, and
   a forward propagation relay device that causes continued propagation of said ideal wave and said distortion wave in an approximately homogeneous medium by a secondary transmission of said received signals, where said continued propagation of said ideal wave and said continued propagation of said distortion wave, and said forward propagation device enables selective measurement of said distortion wave, and a selective measurement device, and
   a device to produce correction signals from results of said selective measurement, and a device to retain signal replicas of said received signals, and
   a device to apply said correction signals to said signal replicas to suppress effects of said distortion waves, and
   a device to produce output signals, and
   a device to process output signals to display an image of said image objects.

31. An imaging system according to claim 30 where said continued propagation is modified by a focusing device to enhance accuracy of said correction signals.

32. An imaging system according to claim 30 where said forward propagation relay device is implemented as a computational equivalent to actual propagation.

33. An imaging system according to claim 30 that implements a combination of said forward propagation relay device and a focusing device to enhance accuracy of said correction signals using a computational process that is equivalent to said combination.

34. An imaging system according to claim 30 that is an ultrasonic imaging system.

35. A computer simulation of an imaging system according to claim 30.

36. An imaging system that is as an optical apparatus where receiving enhancements are achieved with optical devices that carry out functions that are approximately equivalent to a receiving system according to claim 30.

37. An imaging system according to claim 30 where said reflected waves are at frequencies that are harmonics of frequencies of signals transmitted by said wave source.

38. An imaging system according to claim 30 where said received signals are at frequencies that arc harmonics of frequencies of signals transmitted by said wave source.

* * * * *